United States Patent [19]
Kuhle

[11] Patent Number: 5,938,635
[45] Date of Patent: *Aug. 17, 1999

[54] BIOPSY NEEDLE WITH FLARED TIP

[76] Inventor: William G. Kuhle, 815 14th St. Apt. A, Santa Monica, Calif. 90403-1759

[ * ] Notice: This patent issued on a continued prosecution application filed under 37 CFR 1.53(d), and is subject to the twenty year patent term provisions of 35 U.S.C. 154(a)(2).

[21] Appl. No.: 08/774,813

[22] Filed: Dec. 30, 1996

[51] Int. Cl.$^6$ .................................................. A61M 31/00
[52] U.S. Cl. ............................................ 604/51; 604/272
[58] Field of Search ...................... 604/49, 51, 272–274; 606/167, 184, 185; 128/749, 751, 754

[56] References Cited

U.S. PATENT DOCUMENTS

| | | | |
|---|---|---|---|
| 2,828,744 | 4/1958 | Hirsh et al. | 604/272 |
| 2,830,587 | 1/1958 | Everett | 128/221 |
| 3,090,384 | 4/1963 | Baldwin | 128/221 |
| 3,289,675 | 12/1966 | Dunmire | 128/221 |
| 4,306,570 | 12/1981 | Matthews | 128/754 |
| 4,976,684 | 12/1990 | Broadmax, Jr. | 604/51 |
| 5,217,476 | 6/1993 | Wishinsky | 606/167 |
| 5,234,438 | 8/1993 | Semrad | 606/108 |
| 5,290,267 | 3/1994 | Zimmermann | 604/272 |
| 5,304,141 | 4/1994 | Johnson et al. | 604/158 |

OTHER PUBLICATIONS

"Deflection of Spinal by G.B. Drummond et al Needles by the Bevel", Anaesthesia, vol. 35, pp. 854–857 (1980).
"The Bevel and Deflection by E.L. Glazener of Spinal Needles", Anesth Analg, vol. 62, p. 371 (1983).

*Primary Examiner*—John D. Yasko
*Assistant Examiner*—Deborah Blyveis
*Attorney, Agent, or Firm*—Morrison :& Foerster LLP

[57] ABSTRACT

An apparatus and method for performing percutaneous needle biopsies under direct visualization by medical imaging technologies is provided. The apparatus is a biopsy needle comprised of a shaft, a tip which is flared in dimension with respect to the diameter of the shaft, and a longitudinal bevel which imposed on the tip. The shaft and flared tip with bevel are connected as a single unit and the shaft is adaptable for coupling to a needle hub. The flared tip of the needle causes the needle to travel naturally in an arc as the needle is pushed through tissue. This feature is advantageous because obstacles can be avoided and errors in positioning between the needle and the needle's target can be easily corrected by appropriate choice of arcs. The method for advancing the needle into a target or around an obstacle is comprised of combinations of both linear and arcing trajectories. Linear trajactories are obtained either by continuous rotation of the needle about its long axis as the needle is advanced into tissue or by stepwise rotations of the needle about its long axis as the needle is advanced into tissue. An arcing trajectory is obtained by rotating shaft of the needle, and hence the bevel, into an appropriate angular position, holding fixed this particular angular displacement, and then advancing the needle into tissue. An arcing trajectory will result.

30 Claims, 5 Drawing Sheets

| Design Parameter | Example Measurement (IN.) |
|---|---|
| a | 0.0125 |
| b | 0.050 |
| c | 0.050 |
| Ddistal | 0.025 |
| e | 0.050 |
| t | 0.006 |
| r | 0.50 |

Table 1

| Design Parameter | Example Measurement (IN.) |
|---|---|
| a | 0.0125 |
| b | 0.050 |
| c | 0.050 |
| Ddistal | 0.025 |
| e | 0.050 |
| t | 0.006 |
| r | 0.50 |

Table 1

| Design Parameter | Example Measurement (IN.) |
|---|---|
| Ddistal | 0.025 |
| Dprox | 0.050 |
| t | 0.006 |

Table 2

BIOPSY NEEDLE WITH FLARED TIP

BACKGROUND OF THE INVENTION

1. Field of Invention

The present invention relates to biopsy needles which, under the guidance of medical imaging, are used to obtain tissue samples from lesions or drain fluid collections within the body.

2. Description of the Related Art

A frequent procedure in medicine is puncturing the skin with a needle and guiding the needle, using various imaging techniques, into a desired location within the body, typically for purposes of biopsy, fluid drainage, or catheter placement. In medicine, such a procedure is termed a percutaneous needle biopsy. With the advent of cross-sectional imaging techniques such as computed tomography, magnetic resonance imaging, and ultrasound, the use of these percutaneous image-guided procedures has increased dramatically.

Special needles, termed biopsy needles, are used for such procedures. These needles typically consist of a long, thin cylindrical tubular stainless steel shaft with a coaxial cylindrical bore, a central removable stylet (which occupies the bore when the needle is being placed into the body in order to prevent plugs of tissue from accumulating in and obstructing the bore), and an acute needle tip formed by a bevel imposed on the end of the shaft and accompanying stylet. Once the needle is in good position, the stylet is removed, thus exposing the bore of the needle to the target. This exposure allows a sample of tissue from the target to be obtained if the target is solid. If the target is a fluid collection, the fluid can be sampled and drained, if necessary.

Prior-art biopsy needles, as described above, are advanced into the target under direct visualization. However, when using such conventional needles, hitting the target during a procedure can be difficult if the target is small and/or deep within the body or if a direct linear path to the target is unavailable due to an obstructing object, such as a bone, vital organ, or major blood vessel.

When aiming for small, deep targets, even minor errors in the needle's initial direction can cause wide errors in needle tip position when the needle has reached the level of depth of the target. When this situation occurs, a significant length of the needle is withdrawn (typically) and the needle is then redirected and readvanced, hopefully providing a more accurate placement of the needle.

Lack of precise control of the needle during its placement is disadvantageous for several reasons. First, lack of precise control of the needle tip extends the time of the procedure. This is bad as gravely ill, very young or very old patients are typically unable to tolerate extended procedural times. Such patients are able to cooperate only to a limited extent with instructions such as lying flat, remaining motionless and holding the breath. Also, increased procedural times tie up the scanning machine, preventing the examination of other patients, thus indirectly increasing costs. Rates of complications increase both with extended procedural times and with multiple needle passes through the body. Common complications include bleeding (especially if the patient has a bleeding disorder or is on anticoagulant medication), collateral tissue damage, collapsed lung (in upper abdominal procedures), and pain. Increased doses of sedatives and narcotic analgesics may also be necessary for such extended procedures. Finally, some lesions are inaccessible using conventional biopsy needles as such lesions may only be accessible via nonlinear paths. Conventional biopsy needles are made to travel in linear trajectories.

The design of prior-art biopsy needles predate the advent of digital cross-sectional imaging. Not having the anatomic detail now available in modern imaging machines, steerable needles with precise control of the needle tip were not of interest; after all, if the anatomic details were unavailable, why would it be important to design a needle to avoid critical structures if those structures could not be visualized anyway. In fact, a design criterion for needles was that the needle travel in a straight path after introduction into the body. U.S. Pat. No. 2,830,587 (Everett, Apr. 15, 1958) describes various designs of needle shafts which are oval or elliptical in cross-section, the major axis of which is contained within an axial plane that also contains the tip. This arrangement causes the shaft to be more "resistant to bending" in this plane. With current imaging technologies, however, it is advantageous to have the needle travel along nonlinear paths such that critical structures are avoided and to have fine control over the needle tip so that small, deep lesions are more easily accessed.

Despite modern imaging technologies, reliance on conventional, prior-art biopsy needles in percutaneous interventional procedures with their attendant problems, as described above, continues.

SUMMARY OF THE INVENTION

To overcome the disadvantages of the prior art, the present invention provides an apparatus and method for performing improved percutaneous needle biopsies. The apparatus is a long, thin, flexible biopsy needle comprising (1) a shaft which may be tubular (cylindrical) or may taper with increasing distal extent of the shaft, (2) a tip which is flared (that is, expanded in diameter) with respect to the diameter of the shaft, and (3) a bevel which is longitudinally imposed on the tip and which may be convex, flat, or concave in profile. As the needle is advanced through tissue, the flared needle tip causes the needle to curve away in a direction backwards and away from the bevel. The method of using the apparatus is as follows. To cause the needle to travel in a linear direction, the needle is rotated about the shaft's long axis simultaneous with the advancement the needle deeper into tissue. To cause the needle to travel in an arc, the direction of the desired arc is first ascertained, and the bevel of the needle is rotated into a position such that the bevel faces away from the desired direction of the arc. While holding fixed the direction of the bevel, the needle is then advanced through tissue, and the needle will then naturally deflect into the arc as desired. By using a combination of both linear and arcing trajectories, the needle is guided into a target or around an obstacle.

Accordingly, several objects and advantages of the present invention include, without limitation:

(a) to provide more precise control of the needle's tip, thus allowing both greater and easier access to targets within the body of a patient;

(b) to decrease the time of percutaneous image-guided procedures which use long, flexible biopsy needles;

(c) to decrease the rate of complications of percutaneous procedures which use flexible biopsy needles.

Still further objects and advantages will become apparent from a consideration of the ensuing description and drawings.

BRIEF DESCRIPTION OF THE DRAWINGS

FIGS. 6a and 6b are side and bottom views, respectively, of a third needle-shaft embodiment while

DETAILED DESCRIPTION OF THE INVENTION

The present invention provides a biopsy needle for achieving greater control over the trajectory, and hence placement, of the needle. For purposes of explanation, specific details are described to provide a thorough understanding of the present invention. However, those skilled in the art will recognize that the invention may be practiced without these details. In other instances, well known elements, devices, process steps and the like are not set forth in detail in order to avoid unnecessarily obscuring the present invention.

The various embodiments of the biopsy needle tip and shaft of the present invention, as described below, are constructed as a single, integral unit and are made of either metallic, composite or polymeric material. If the needle is metallic it can be fabricated from metal tubing. If the needle is polymeric or composite, it can be cast into its form, or it can be machined from composite or polymeric tubing. The proximal end of the shaft is adapted for coupling to a needle hub for the attachment of the needle to a syringe or other device.

For purposes of convenience and clarity in describing the invention, this detailed description refers to various "section (s)." Note, however, that the use of the term "sections" does not imply that such sections are manufactured individually with subsequent assembly of the needle from these sections. Rather, the needle is contructed as an integral unit and not necessarily from a concatenation of various discretely-manufactured pieces.

Figure 1A:
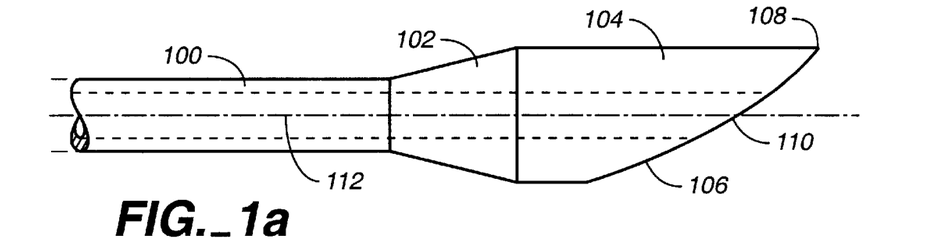
FIGS. 1a and 1b represent side and bottom cross-sectional views, respectively, of one embodiment of a needle tip.
Figure 1B:
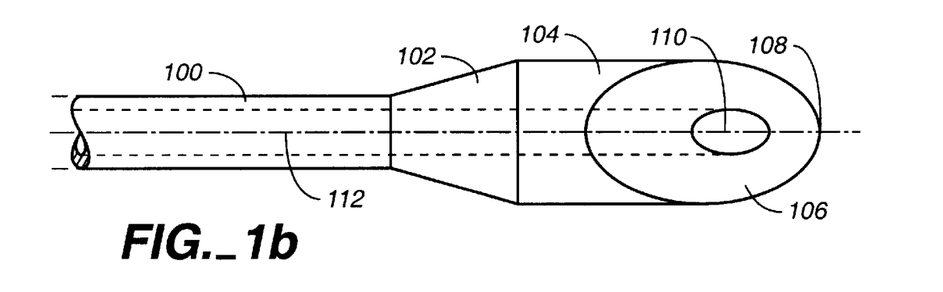

A first embodiment of a biopsy needle tip of the present invention is depicted in FIGS. 1a and 1b. The section 100 of the needle is partially shown and represents the continuation of the most distal end of the shaft of a biopsy needle. Section 100 has a central cylindrical bore 112 as represented by two parallel evenly-dashed lines.

The tip of the biopsy needle is defined as sections 102 and 104 together. Section 102, which is a frustrum, is connected to section 100. The long axis of middle section 102 is colinear with that of section 100 and the bore 112 continues in an uninterrupted linear course through section 102. The junction of section 100 with section 102 is smooth. Although FIGS. 1a and 1b depict the diameter of section 102 expanding (flaring) linearly with increasing distal extent, those skilled in the art will recognize that it need not necessarily flare linearly; rather, any smoothly-expanding design for section 102 will suffice. Section 104 is shown as a cylindrical tube having a longitudinal bevel 106 imposed at its distal end. Note that bevel 106 has a slight convexity as shown in FIG. 1a. The diameter of section 104 matches the diameter of the distal portion of section 102, and section 104 is smoothly and colinearly connected to the distal end of section 102. Again, although FIGS. 1a and 1b depict section 104 to be a cylinder with a bevel, those skilled in the art will recognize that section 104 need not necessarily be cylindrical with a bevel; rather, a smoothly expanding (flaring) configuration with an imposed bevel can also suffice.

The bore 112 continues in an uninterrupted linear course through section 104 and terminates in lumen opening 110. FIGS. 1a and 1b show that bevel 106 terminates in a distal point 108.

Figure 1C:
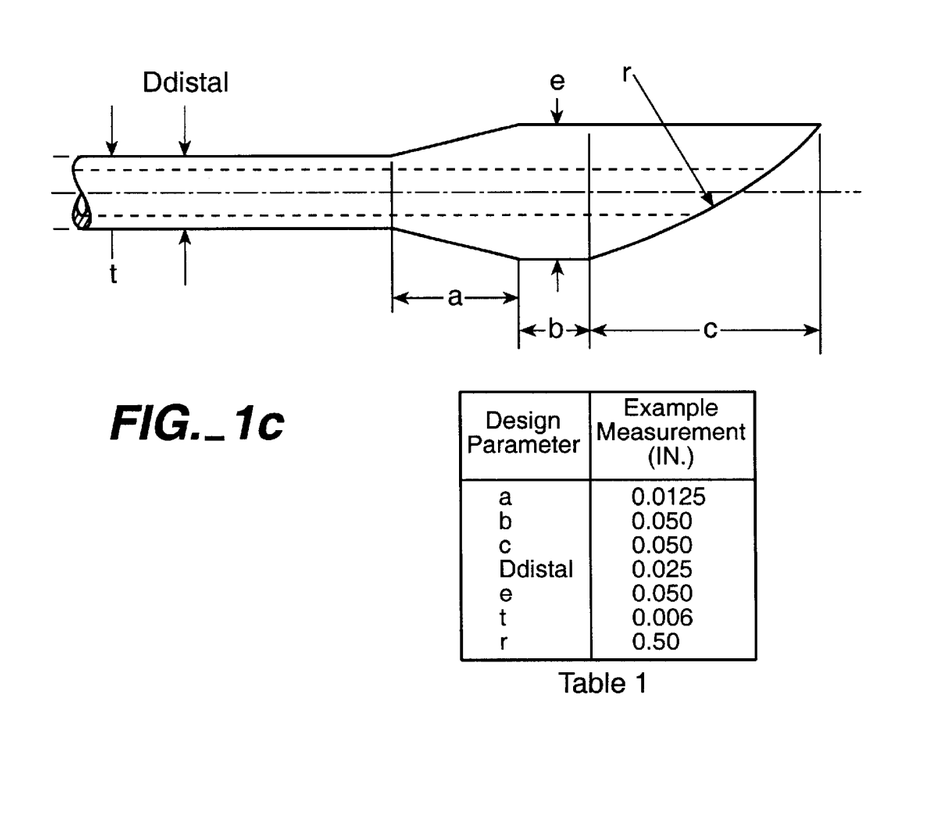
FIG. 1c represents an example of a set of dimensions for a needle-tip embodiment shown in FIGS. 1a and 1b.
Figure 2A:
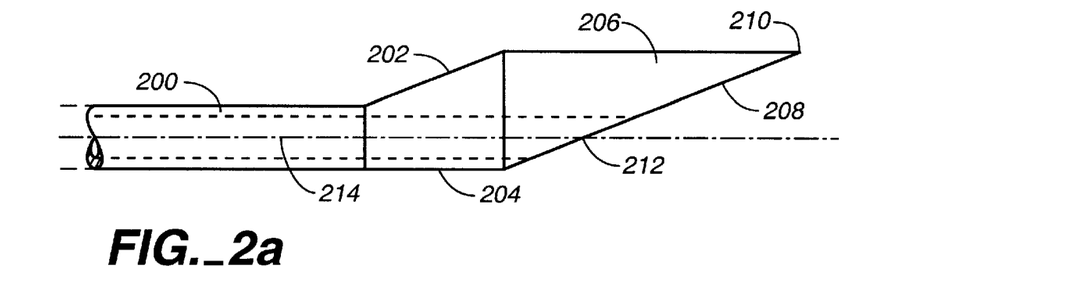
FIGS. 2a and 2b represent side and bottom views, respectively, of a second needle-tip embodiment of the invention.
Figure 2B:
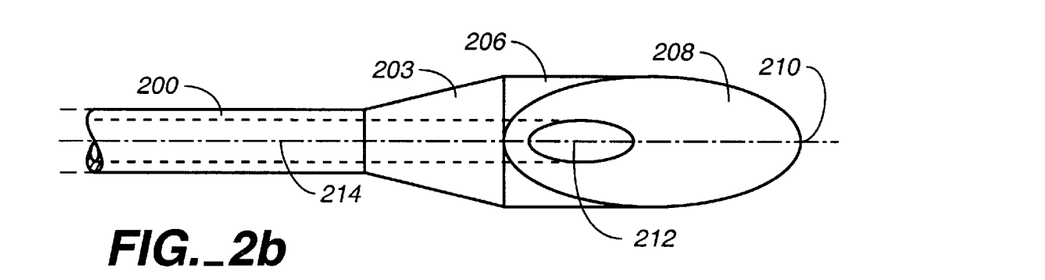

A second embodiment is shown in FIG. 2. The section 200 in FIG. 2 is identical to section 100 of FIG. 1. The embodiment of FIG. 2 contains a middle section 203 which is smoothly and colinearly affixed to the distal end of section 200 and has the projection of a frustrum when viewed from the bottom (FIG. 2b). However, when viewed from the side (FIG. 2a), an inferior edge 204 of section 203 is colinearly continuous with an inferior edge of section 200. An edge 202, which is the superior edge of section 203 when viewed from the side, expands linearly outwards with increasing distal extent of section 203, as shown in side view FIG. 2a. Again, those skilled in the art will recognize that the expanding portion of section 203 need not necessarily flare linearly; rather, any smoothly-expanding design will suffice. End section 206 is a cylindrical tube having a longitudinal flat bevel 208 imposed at its distal end. The diameter of section 206 matches the diameter of the distal end of section 203, and section 206 is smoothly and colinearly affixed to the distal end of section 203. Cylindrical bore 214 continues in an uninterrupted linear course through sections 200, 203, and 206 and terminates in lumen opening 212. Bevel 208 terminates in a distal point 210.

Figure 3A:
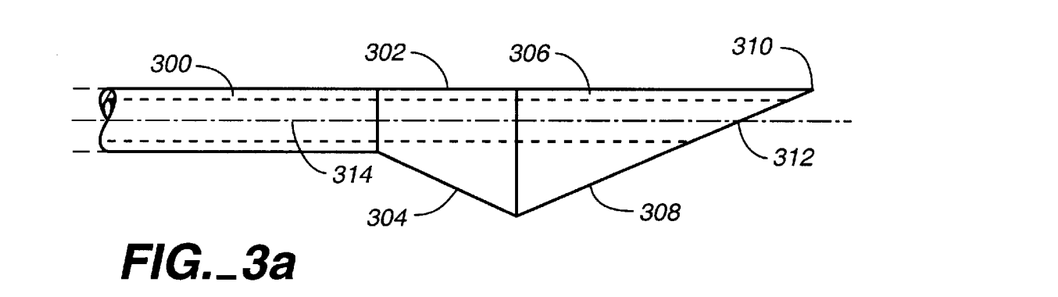
FIGS. 3a and 3b represent side and bottom views, respectively, of a third needle-tip embodiment of the invention.
Figure 3B:
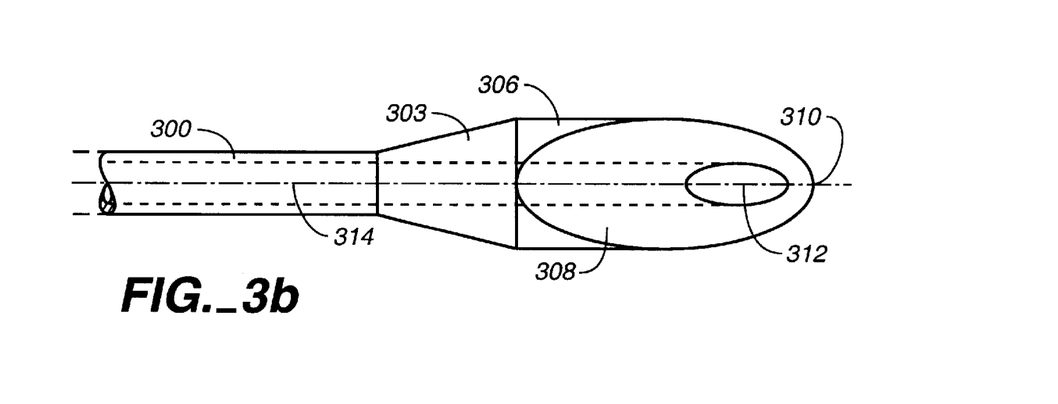

A third embodiment is shown in FIG. 3. The section 300 in FIG. 3 is identical to section 100 of FIG. 1. The embodiment of FIG. 3 contains a middle section 303 which has the projection of a frustrum when viewed from the bottom (FIG. 3b). However, when viewed from the side (FIG. 3a), a superior edge 302 of section 303 is colinearly continuous with a superior edge of section 300. An edge 304 which is the inferior edge of section 303 when viewed from the side expands linearly outwards with increasing distal extent of section 303, as shown in side view FIG. 3a. Again, those skilled in the art will recognize that the expanding portion of section 303 need not necessarily flare linearly; rather, any smoothly-expanding design will suffice. End section 306 is a cylindrical tube having a longitudinal bevel 308 at its distal end. The diameter of section 306 matches the diameter of the distal end of section 303, and section 306 is smoothly and colinearly affixed to the distal end of section 303. Cylindrical bore 314 continues in an uninterrupted linear course through sections 300, 303, and 306 and terminates in lumen opening 312. Bevel 308 terminates in a distal point 310.

TABLE 1 reports (and FIG. 1c illustrates by way of example) a set of example dimensions for the design parameters a (length of middle section 102), b (length of the unbeveled portion of end section 104), c (length of the beveled portion of end section 104), Ddistal (outer diameter of section 100), e (outer diameter of end section 104), t (thickness of the wall of section 100), and r (radius of curvature of the lengthwise bevel of end section 104). However, other needle dimensions are also conceivable, with corresponding changes of linear (or otherwise) scaling in these design parameters.

The bevel of each embodiment can be chosen as either convex, flat, or concave. These types of bevel can modulate as desired the degree of responsiveness of the needle tip to a lateral deflecting force (as described in the Operation of the Invention section).

Figure 4A:
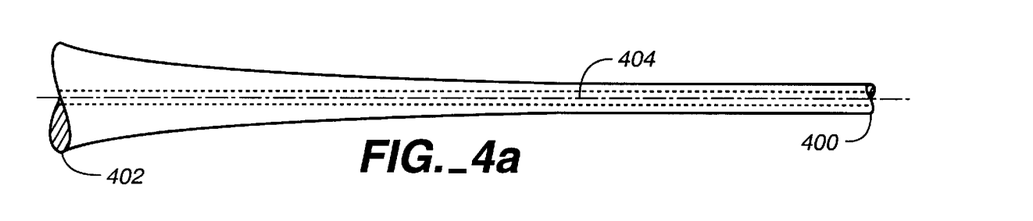
FIG. 4c represents an example of a set of cross-sectional dimensions for a needle-shaft embodiment shown in FIGS. 4a and 4b.
Figure 4B:
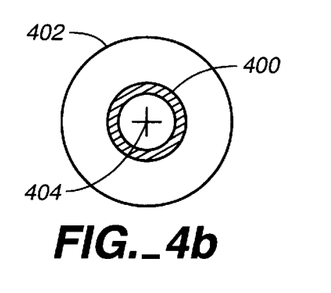

Regarding the shaft of the needle of the present invention, three embodiments are described. Side and end views of the first embodiment of the shaft are shown in FIGS. 4a and 4b, respectively. The shaft of the present invention exhibits cylindrical symmetry about its long axis, and as indicated in FIG. 4b, any cross-section of the shaft which is perpendicular to the shaft's long axis is circular. The long axis of the shaft is defined as an axis which is positioned down the center of cylindrical bore 404 of the shaft. The proximal end 402 of the needle shaft has a larger diameter than that of distal end 400. Between proximal end 402 and distal end 400, the diameter of the shaft smoothly tapers with increasing distal extent of the shaft. In the first embodiment this taper is linear although other nonlinearly-tapering shaft designs are conceivable.

Figure 5A:
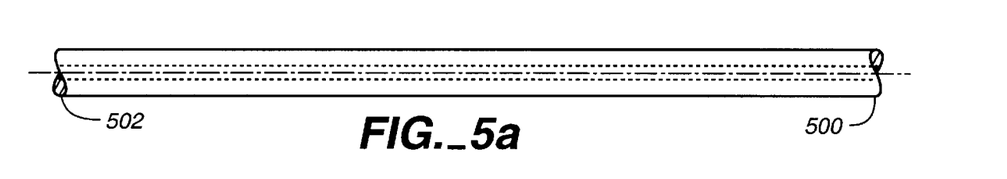
FIG. 5a and 5b are side and bottom views, respectively, of a second needle-shaft embodiment.
Figure 5B:
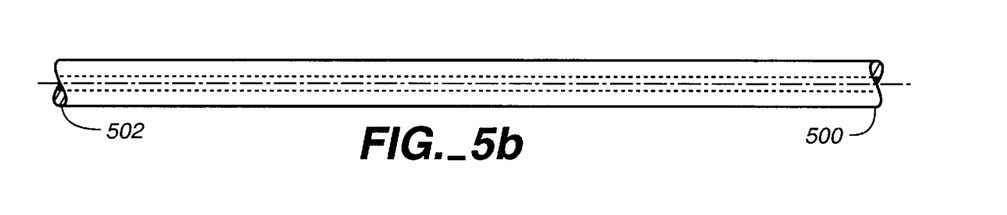

A second embodiment has proximal end 502 and distal end 500 with the same diameter (no taper of the shaft). Any cross-section of the shaft which is perpendicular to the shaft's long axis is circular. Bottom and side views of this embodiment are shown in FIGS. 5a and 5b, respectively.

Figure 6A:
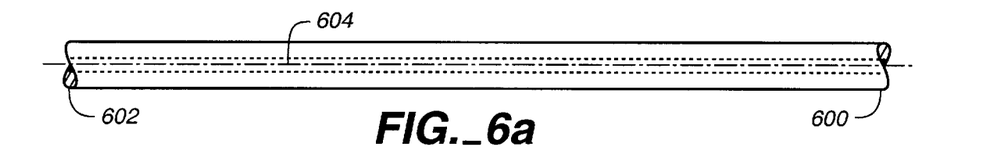
Figure 6B:
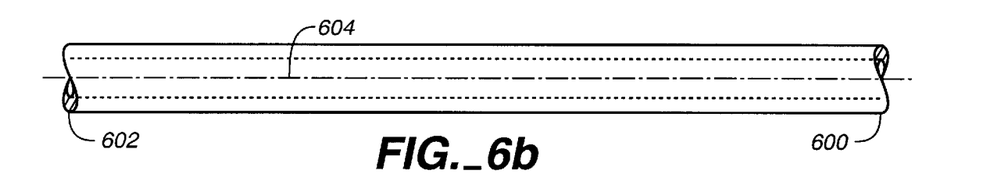
Figure 6C:
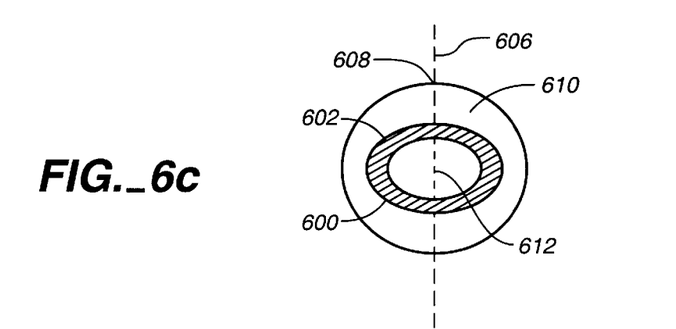
FIG. 6c is an end view of the shaft of FIGS. 6a and 6b coupled to the first embodiment of the needle tip.

A third shaft embodiment has a cross-section which is oval in any cross-sectional plane perpendicular to the long axis of the shaft, as shown in FIGS. 6a, 6b, and 6c. A shaft of oval cross-section is more resistant to bending in the plane containing the major axis of the oval than in the plane containing the minor axis of the oval. Such a shaft may or may not be tapered. FIGS. 6a and 6b show side and bottom views, respectively, of a non-tapered embodiment of an oval shaft. 602 is the proximal end, 600 is the distal end of the shaft, and 604 is the cylindrical bore centered on the long axis of the shaft. FIG. 6c is an end view of a shaft with an oval cross-section connected to the first embodiment of a needle tip (as shown in FIGS. 1a and 1b). The minor axis 612 of the shaft of this embodiment is contained within an axial plane 606 which bisects the needle tip 610 into two symmetrical halves. 608 represents the point of the needle tip. This configuration is of advantage as the needle will preferentially bend into an arc which is contained within the aforementioned plane of bisection. Carefully note the difference between this configuration and that of U.S. Pat. No. 2,830,587 (Everett, Apr. 15, 1958). Everett's patent describes a shaft of oval or elliptical cross-section in which the major axis of this oval or elliptical cross-section lies in the axial plane which bisects the needle's tip. This design was meant to resist bending in the bisecting axial plane. By causing the minor axis, rather than the major axis, to lie within the aforementioned plane, the design of the present invention promotes, rather than resists, bending in this plane.

Figure 4C:
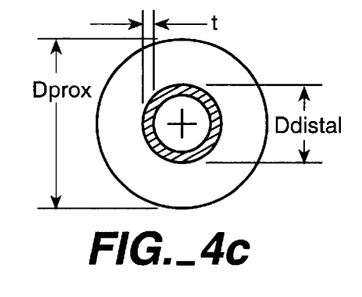

The previously described biopsy needle tips of the present invention are colinearly and smoothly attached (1) to distal end 400 (FIG. 4) of the first embodiment of the shaft, or (2) to distal end 500 of FIG. 5, or (3) to distal end 600 of FIG. 6. The flow bore of the shaft aligns colinearly with that of the needle tip. TABLE 2 reports (and FIG. 4c illustrates by way of example) a set of example dimensions for the design parameters Dprox (the proximal diameter of the needle's shaft) and Ddistal (the distal diameter of the needle's shaft). However, other needle shaft dimensions are also conceivable, with corresponding changes of linear (or otherwise) scaling in these design parameters.

Operation of the Invention

Figure 7:
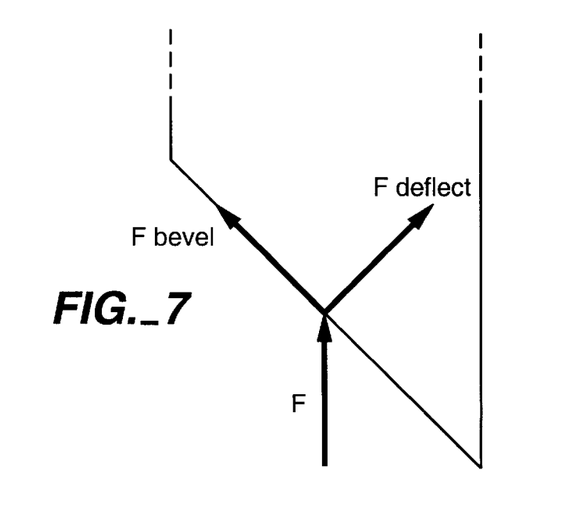
FIG. 7 is a schematic side view of the force experienced by a needle tip as the needle is driven into tissue, and this force's decomposition along two different axes.

A biopsy needle with a geometrically-symmetric tip experiences no asymmetries in the forces the tip sees as the needle is advanced into tissue; therefore, the following analysis does not apply to this type of needle. Only biopsy needles with an asymmetric needle tip will be subject to a lateral deflecting force, and the physical basis by which asymmetry in the needle tip affects the needle's trajectory is as follows. FIG. 7 shows that advancing a beveled needle tip in tissue subjects that tip to a force F which can be resolved into two directions. One force component Fbevel is directed along the length of the bevel, and the other force component Fdeflect is directed perpendicular to the bevel. Fdeflect causes the needle tip to deflect laterally and into a curved trajectory. It can be shown that Fdeflect is proportional to $(\pi2)/4$, where e is the diameter of the needle tip as shown in FIG. 1**c and also to the tissue pressure generated at the needle tip as the needle is advanced (of course, force equals the product of the area with the pressure). Therefore, the amount of lateral deflecting force increases with increasing diameter e (that is, increasing the amount of flare) of the needle tip.

Figure 8A:
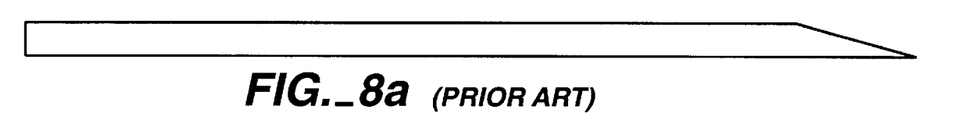
FIGS. 8a and 8b represent side and bottom views of a prior-art biopsy needle tip and shaft.
Figure 8B:
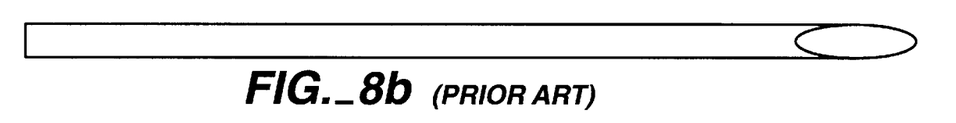

Side and bottom views of prior-art designs of beveled-tip needles are shown in FIGS. 8a and 8b, respectively. Prior-art biopsy needles with simple beveled tips do not generate much lateral deflecting force because the area of the beveled tip is relatively small with respect to the cross-sectional area of the shaft. For such prior-art needles, this situation is, in fact, desirable as the physician does not want the needle to deflect laterally as the needle is advanced. In order to generate larger deflecting forces at the needle tip, a simple solution is to increase the surface area of the needle's beveled tip. However, in order to maintain the needle's flexibility and responsiveness to this increased lateral deflecting force, the diameter of the shaft of the needle must remain relatively narrow with respect to the tip. If the diameter of the needle's tip matches that of the shaft (as in prior-art needles), the needle will not respond well to the larger Fdeflect forces generated due to an increased stiffness of the relatively larger shaft.

As shown in FIGS. 1, 2, and 3, the tips of the needles of the present invention are flared with respect to the distal shaft diameter, thus giving the needle tip a larger surface area for generating lateral deflecting forces. Because the diameter of the distal shaft of needle shaft remains relatively narrow, the biopsy needle of the present invention is able to flex more easily in response to the increased lateral deflecting forces. With respect to the present invention's first embodiment of the needle shaft of FIG. 4, the thicker needle shaft proximally causes the shaft to have increased resistance to bending for that portion of the needle which is outside the body. Increased resistance to bending at the proximal portion of the shaft allows for greater axial-driving forces to be applied to the needle without causing the proximal portion of the needle shaft to flex undesirably.

Use of the biopsy needle of the present invention is as follows. The needle's point is first used to puncture the skin.

To advance the needle along a linear trajectory, the entire needle is continuously rotated either clockwise or counterclockwise around its long axis as the needle is pushed deeper through tissue into the body. This rotatory motion causes the lateral deflecting force to average out to zero over a 360 degree rotation, thus preventing the needle from preferentially deviating in any one direction. A second method to generate a linear trajectory is to (1) hold fixed the direction of the bevel, (2) push the needle deeper through tissue a short distance, (3) rotate the bevel 180 degrees, (4) push the needle deeper through tissue another short distance, (5) repeat steps (3) and (4) as many times as needed. This method generates a trajectory of numerous short but oppositely-directed arcs, thus effectively producing a linear trajectory.

Figure 9:
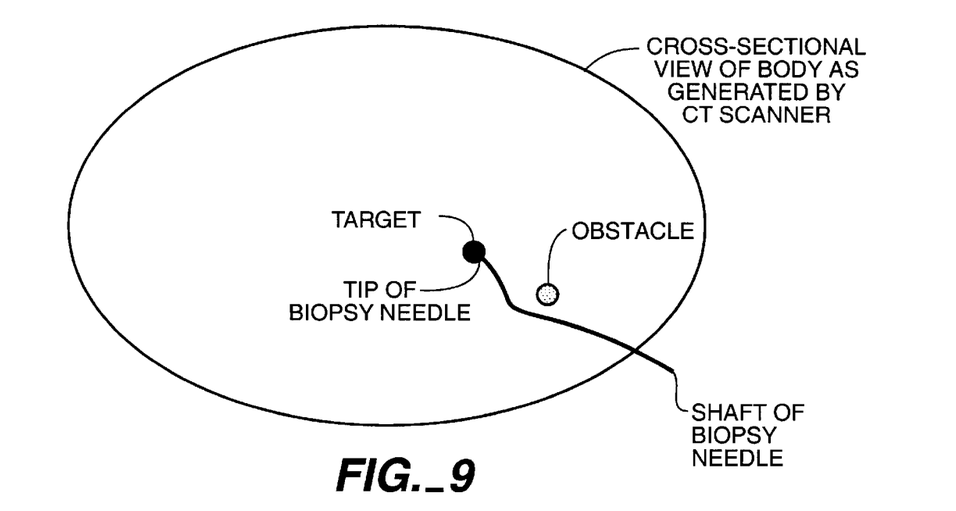
FIG. 9 represents a side view of the present invention deflected around an obstacle within the body.

To avoid an obstacle or to correct for errors in the position of the needle tip with respect to a target, the direction of the desired arc is first ascertained. Then, while holding the depth of the needle fixed, the bevel of the needle is rotated into a position such that the bevel faces away from the desired direction of the arc. Next, while holding fixed the direction of the bevel, the needle is then advanced through tissue, and the needle will then naturally deflect into the desired arc, thus avoiding an obstacle or correcting positioning error. For example, if the desired arc is a curve upwards towards the patient's head, the needle's shaft is first rotated into a position such that the bevel faces the patient's feet. Then, advancing the needle will cause the needle's tip to curve in an upward arc. By using a combination of linear and arcing trajectories, the needle is guided into the target. If an obstacle was avoided, the original path is resumed by reorienting the bevel's direction 180 degrees opposite of the first fixed-bevel orientation and advancing the needle, thus bending the needle back toward its original path. This situation is illustrated in FIG. 9.

Summary, Ramifications, and Scope

From the descriptions above, the advantages of the biopsy needle of the present invention become evident:

(a) Because the needle tip is expanded (flared) with respect to the shaft of the needle, the needle tip experiences increased lateral deflecting forces thus causing the needle tip to naturally curve in a direction away from the bevel of the needle's tip.

(b) The relatively thin shaft of the present invention offers decreased resistance to lateral bending forces, in comparison to a prior-art needle which has a shaft having the same diameter as the needle's tip. This decreased resistance allows the needle to form an arc relatively easily.

(c) The amount of deflecting forces generated at the needle's tip can be controlled by appropriately selecting the design parameters which affect the area of the bevel of the needle tip. The radius of curvature r of the bevel also influences the sensitivity of the needle tip to lateral bending forces.

(d) A thicker proximal needle shaft allows the needle to sustain greater axial loads and to resist unwanted bending of the portion of the shaft which is outside the body.

Although the invention has been described in conjunction with various embodiments and specificities, such embodiments and specificities should not be construed as limiting the scope of the invention. These descriptions merely provide illustrations of some of the presently preferred embodiments of this invention, and those skilled in the art will appreciate that various modifications and alterations may be made without departing from the spirit and scope of the invention. For example, the needle tip can have, with respect to the diameter of the distal needle shaft, various expansile (flaring) designs. The bevel as imposed on the needle tip may actually be comprised of several planar surfaces of differing obliquity and orientation, yet causing an asymmetrical needle tip, with such planes converging to provide a single point. Additionally, the type of taper of the needle shaft may be nonlinear with increasing distal extent of the shaft. For example, the taper can be a "staircase" in style, with segmental decreases in shaft diameter with increasing distal extent of the shaft. Other types of taper, such as logarithmic, exponential, polynomial, etc. are possible. The cross-sectional shape of the shaft can have shapes other than circular or oval. For example, a cross-sectional shape of an ellipse with its minor axis aligned to lie within an axial plane which bisects the needle tip into two symmetrical halves also permits preferential directional bending of the needle into an arc away from the bevel. In addition, the method for causing the needle to travel in a linear trajectory can be varied. For example, instead of sequentially incrementing the depth of the needle together with sequential 180 degree rotations of the needle shaft, an equivalent, substantially linear trajectory can result from sequential 90 degree rotations when combined with increments in depth. Finally, those skilled in the art will recognise that other needle structures and accompanying methods other than those described herein can be employed to cause a deflecting force to be applied to the needle, thus causing the needle to travel in an arcing trajectory as it is advanced into tissue.

Thus, the scope of the invention should be determined by the appended claims and their legal equivalents, rather than by the examples given.

What is claimed is:

1. A biopsy needle comprising:
   (a) a needle shaft; and
   (b) a needle tip coupled to said needle shaft and flared with respect to said needle shaft, wherein said needle shaft has sufficient resistance to bending to transfer axial driving forces to said needle tip to allow said needle tip to initially penetrate the tissue, and said needle shaft is sufficiently flexible to allow said needle to travel in an arcing trajectory due to a deflection force imposed on said needle tip during advancement of said needle into the tissue.

2. The biopsy needle of claim 1, wherein said needle shaft is straight.

3. The biopsy needle of claim 1, wherein said needle shaft comprises a metallic material.

4. The biopsy needle of claim 1, wherein said needle shaft comprises a polymeric material.

5. The biopsy needle of claim 1, wherein flexibility of said needle shaft is the same during the initial penetration and subsequent advancement of said needle into the tissue.

6. The biopsy needle of claim 1, wherein said needle shaft has sufficient resistance to bending to transfer axial driving forces to said needle tip to allow said needle tip to initially penetrate the tissue without a metal stylet inside said needle shaft.

7. The biopsy needle of claim 1, wherein the arcing trajectory allows said needle tip to bypass an obstructing object within the tissue.

8. A biopsy needle comprising:
   (a) a needle shaft, said needle shaft having a distal end, a proximal end, a long axis, and a plurality of cross-sections which are measured in planes perpendicular to the long axis; and (b) a needle tip flared with respect to said needle shaft and extending from the distal end of said needle shaft, wherein said needle shaft has sufficient resistance to bending to transfer axial driving forces to said needle tip to allow said needle tip to initially penetrate tissue, and said needle shaft is sufficiently flexible to allow said needle to travel in an arcing trajectory during advancement of said needle into the tissue, wherein the flaring of said needle tip enhances arcing of said needle within the tissue.

9. The biopsy needle of claim 8, wherein said needle tip ends in a bevelled point.

10. The biopsy needle of claim 9, wherein said bevel is convex.

11. The biopsy needle of claim 9, wherein said bevel is flat.

12. The biopsy needle of claim 9, wherein said bevel is concave.

13. The biopsy needle of claim 8, wherein said needle shaft is tapered, with the proximal end of said needle shaft larger in cross-sectional area than the distal end of said needle shaft.

14. The biopsy needle of claim 8, wherein the cross-sections of said needle shaft are circular.

15. The biopsy needle of claim 8, wherein cross-sections of said needle shaft are symmetrical and noncircular, and resistance to bending of said needle shaft is least in a plane which contains the long axis of said needle shaft and which bisects said needle tip into symmetrical halves.

16. The biopsy needle of claim 8, wherein said needle shaft is straight.

17. The biopsy needle of claim 8, wherein said needle shaft comprises a metallic material.

18. The biopsy needle of claim 8, wherein said needle shaft comprises a polymeric material.

19. The biopsy needle of claim 8, wherein flexibility of said needle shaft is the same during the initial penetration and subsequent advancement of said needle into the tissue.

20. The biopsy needle of claim 8, wherein said needle shaft has sufficient resistance to bending to transfer axial driving forces to said needle tip to allow said needle tip to initially penetrate the tissue without a metal stylet inside said needle shaft.

21. The biopsy needle of claim 8, wherein the enhanced arcing allows said needle tip to bypass an obstructing object within the tissue by detouring around the obstructing object.

22. A method for guiding a biopsy needle through tissue of a body and into a target, the method comprising the steps of:

(a) inserting a flared tip of said biopsy needle into the tissue; and (b) advancing said flared tip of said needle into the tissue, thereby causing said needle to travel in an arcing trajectory.

23. The method of claim 22, further comprising the step of advancing said needle into tissue while rotating said needle about its long axis so that a trajectory of said needle is substantially linear.

24. A biopsy needle comprising:

(a) a needle shaft; and (b) a needle tip coupled to said needle shaft, wherein said needle tip is flared with respect to said needle shaft to allow said needle to travel in an arcing trajectory due to a deflection force imposed on said needle tip when the needle is advanced into the tissue, wherein said needle shaft is bendable during initial insertion of said needle tip into the tissue.

25. The biopsy needle of claim 24, wherein said needle shaft is straight.

26. The biopsy needle of claim 24, wherein said needle shaft comprises a metallic material.

27. The biopsy needle of claim 24, wherein said needle shaft comprises a polymeric material.

28. The biopsy needle of claim 24, wherein flexibility of said needle shaft is the same during the initial insertion and subsequent advancement of said needle into the tissue.

29. The biopsy needle of claim 24, wherein said needle shaft has sufficient resistance to bending to transfer axial driving forces to said needle tip to allow said needle tip to initially penetrate the tissue without a metal stylet inside said needle shaft.

30. The biopsy needle of claim 24, wherein the flared tip allows said needle to travel in an arcing trajectory around an obstructing object.

* * * * *